United States Patent
Hu

(10) Patent No.: US 9,145,359 B2
(45) Date of Patent: Sep. 29, 2015

(54) CYCLIC PROCESS FOR THE PRODUCTION OF TAURINE FROM MONOETHANOLAMINE

(71) Applicant: Songzhou Hu, North Brunswick, NJ (US)

(72) Inventor: Songzhou Hu, Princeton, NJ (US)

( * ) Notice: Subject to any disclaimer, the term of this patent is extended or adjusted under 35 U.S.C. 154(b) by 4 days.

(21) Appl. No.: 13/998,958

(22) Filed: Dec. 30, 2013

(65) Prior Publication Data

US 2015/0183731 A1    Jul. 2, 2015

(51) Int. Cl.
  *C07C 303/02* (2006.01)
  *C07C 303/42* (2006.01)
  *C07C 303/24* (2006.01)

(52) U.S. Cl.
  CPC ............. *C07C 303/02* (2013.01); *C07C 303/24* (2013.01); *C07C 303/42* (2013.01)

(58) Field of Classification Search
  CPC .. C07C 303/02; C07C 303/42; C07C 303/28; C07C 303/44
  See application file for complete search history.

(56) References Cited

U.S. PATENT DOCUMENTS 8,609,890  B1    12/2013  Hu

FOREIGN PATENT DOCUMENTS

| CN | 101100449 | 1/2008 |
| CN | 102633689 | 8/2012 |
| JP | S608254 | 1/1985 |

*Primary Examiner* — Sun Jae Yoo

(57) ABSTRACT

A method is disclosed for the production of taurine in high yield by a cyclic process of reacting monoethanolamine, sulfuric acid, and ammonium sulfite in the presence of additives to inhibit the hydrolysis of 2-aminoethyl hydrogen sulfate intermediate. The cyclic process is economical and little waste is generated.

4 Claims, 2 Drawing Sheets

CYCLIC PROCESS FOR THE PRODUCTION OF TAURINE FROM MONOETHANOLAMINE

TECHNICAL FIELD

This invention relates to a cyclic process for preparing taurine from monoethanolamine by way of 2-aminoethyl hydrogen sulfate intermediate in high yield which is economical and in which little waste is generated.

BACKGROUND OF THE INVENTION

Taurine can be referred to as 2-aminoethanesulfonic acid and is of the formula $H_2NCH_2CH_2SO_3H$. Taurine is an extremely useful compound because it per se has such pharmacological effects as detoxification effect, fatigue-relieving effect and nourishing and tonifying effect. As a result, taurine finds wide applications as an essential ingredient for human and animal nutrition.

Numerous chemical methods have been known in the prior arts for preparing taurine and related derivatives. The following two methods have been used in industry to manufacture over 50,000 tons of taurine per year, starting from ethylene oxide (the EU process) and monoethanolamine (the MEA process).

According to the EO process, EO is reacted with sodium bisulfite to obtain sodium isethionate, which undergoes ammonolysis to yield sodium taurinate. Neutralization with sulfuric acid results in a mixture of taurine and sodium sulfate.

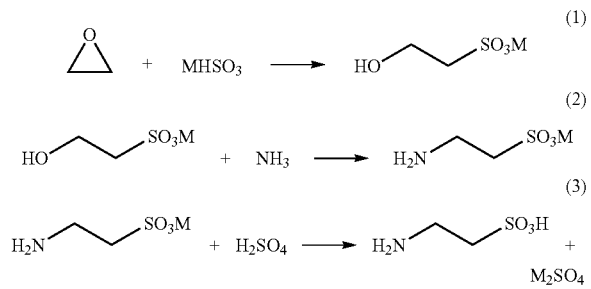

In the reactions, M stands for cations, which can be ammonium, lithium, sodium, and potassium.

The EO process has been greatly improved in U.S. Pat. No. 8,609,890 by using sulfur dioxide to neutralize the basic solution of taurinate to recover taurine and to regenerate sodium bisulfite.

The disadvantage of the EU process lies in the problematic quality of the product. More specifically, taurine produced via the EO process is a powder, and tends to form a hard cake over a short period of time during storage (in a matter of weeks), possibly due to the presence of unknown impurities. The process involves some serious hazards from the viewpoint of safety since it uses, as raw material, EO, which has extremely strong toxicity and carcinogenicity and is difficult to transport and handle. Moreover, the reaction is carried out at very high temperature (220-280° C.) and pressure (>100 bars).

Starting from MEA, taurine can be prepared by reacting MEA with sulfuric acid to obtain the key intermediate, 2-aminoethyl hydrogen sulfate ester (AES). Subsequent reaction with sodium sulfite yields a complex mixture of taurine, sodium sulfate, sodium sulfite and other impurities.

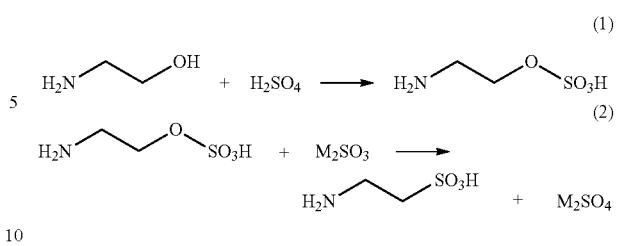

The distinct advantage of the MEA process over the EO process is the exceptional quality of the final product, for the taurine obtained is in the form of needle crystal and shows excellent stability during transportation and storage. The thus obtained taurine shows no sign of caking even over a long period of storage time. An added advantage is the mild processing conditions for the safe operation of the manufacturing plant.

A detrimental disadvantage of the MEA process is its higher production cost over the EO process. The main cause is its much lower production yield, the most improved in the industry being in the range of 55-63%. On the other hand, the yield in the EO process is about 75%.

The disadvantage of the MEA process is further exasperated by the extended heating over a long period of time in the sulfonation stage, typically 35-40 hours, as the reaction between AES and sodium sulfite is extremely slow.

These conventional EO and MEA processes are further complicated by another problem such as the separation of taurine from sodium sulfate, as both processes yield a product mixture of taurine and inorganic salts. Because the solubility of taurine and sodium sulfate is similar at temperature below 40° C., sodium sulfate, having nearly the same solubility from 40 to 90° C., has to be crystallized and removed at above room temperature to prevent taurine from crystallization. Repeated heating and cooling are required to separate these two components.

Still another problem in these conventional industrial processes is the disposal of waste stream, comprising of residual taurine, inorganic salts, and high content of organic materials.

Attempt has been made to lower the production cost for the MEA process by substituting sodium sulfite with less costly ammonium sulfite. The yield is still insufficient at less than 65% to compete with the EO process on an industrial scale. Moreover, the waste stream, rich in ammonium salts, could not be satisfactorily treated. Satisfactory method to separate taurine from ammonium sulfate remains to be developed.

According to a process disclosed in JPS608254, the reaction solution of AES and ammonium sulfite is first evaporated to dry, then hydrochloric acid is added to dissolve taurine. The insoluble inorganic salt is filtered off and then washed with concentrated hydrochloric acid. Afterwards, the mother liquor is concentrated to dry again, followed by addition of ethanol to crystallize taurine. This complicated process cannot thus be considered as an industrial production process.

According to another process described in CN101100449A, the reaction mixture between AES and ammonium sulfite is directly cooled to crystallize taurine. After filtration, crude taurine is refined by recrystallization from distilled water. The mother liquor, comprised of taurine and ammonium sulfate and excess ammonium sulfite, has to be discarded.

CN102633689 describes a process of reacting AES and ammonium sulfite to produce taurine and to remove the byproduct of ammonium sulfate and excess sulfite with calcium hydroxide. The expensive starting material, ammonium sulfite, and valuable byproduct, ammonium sulfate, are turned into a waste mixture of calcium sulfite and calcium sulfate. In addition, residual calcium sulfate is introduced into the product stream, thus making final purification to a product of pharmaceutical grade more difficult.

To ensure a good economy of the process, ammonium sulfate should be recovered with a low content of taurine, in a form suitable for fertilizer production. Hence, it is important to have available a method for efficient separation among taurine, ammonium sulfate, and ammonium sulfite.

It is an object of the present invention to overcome the disadvantages of the known MEA process to produce taurine in high yield which is very economical and to provide, in addition, advantages, which will become apparent from the following description.

It is another object of the present invention to disclose a process for the recovery of ammonium sulfate from an aqueous solution which contains ammonium sulfate and taurine. The recovered ammonium sulfate contains less than 0.5% by weight of taurine, and is suitable for fertilizer production.

It is a further object of the present invention to provide a cyclic process for treating the bleeding waste solution by esterifying the residual MEA with sulfuric acid to AES, which can be then converted to taurine. This cyclic process ensures that little waste is generated in the overall process.

DESCRIPTION OF THE INVENTION

Figure 1:
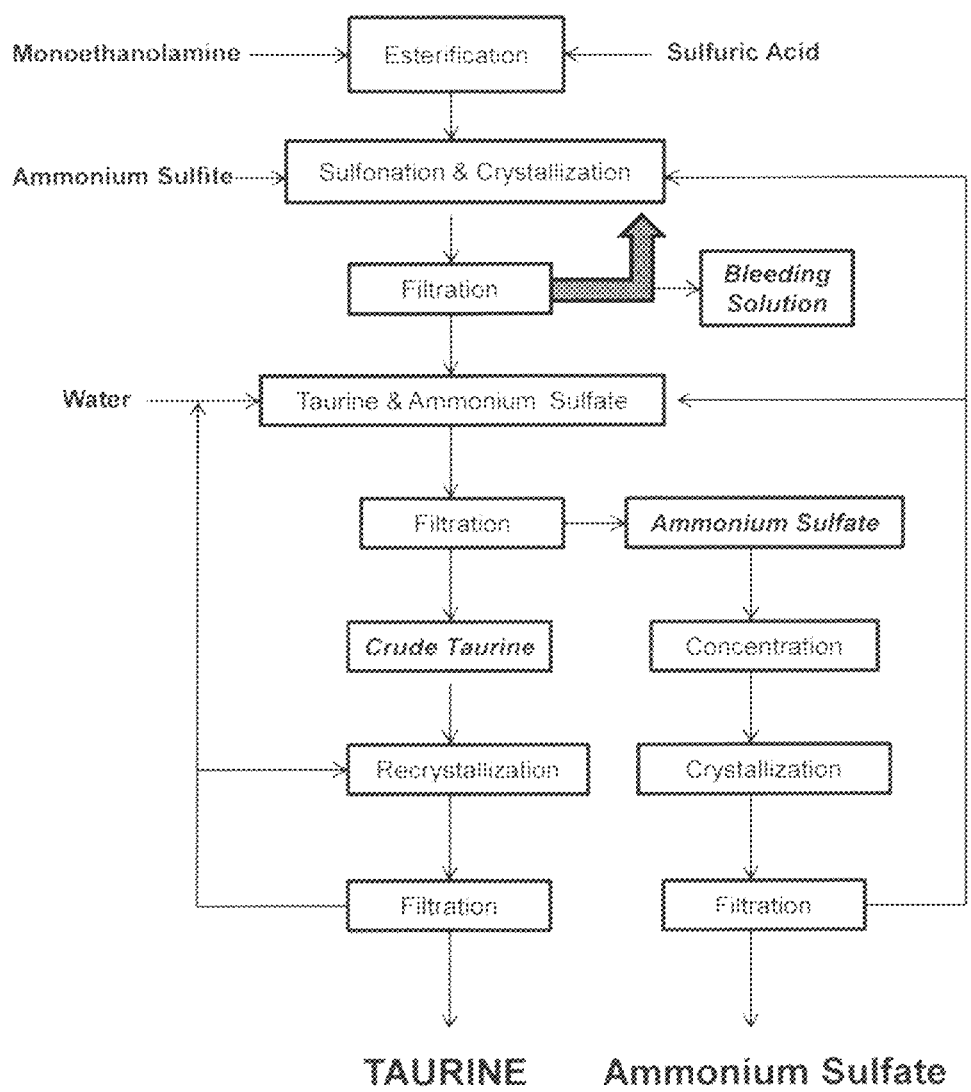
FIG. 1 is a flow chart for producing taurine and ammonium sulfate from MEA, sulfuric acid and ammonium sulfite.
Figure 2:
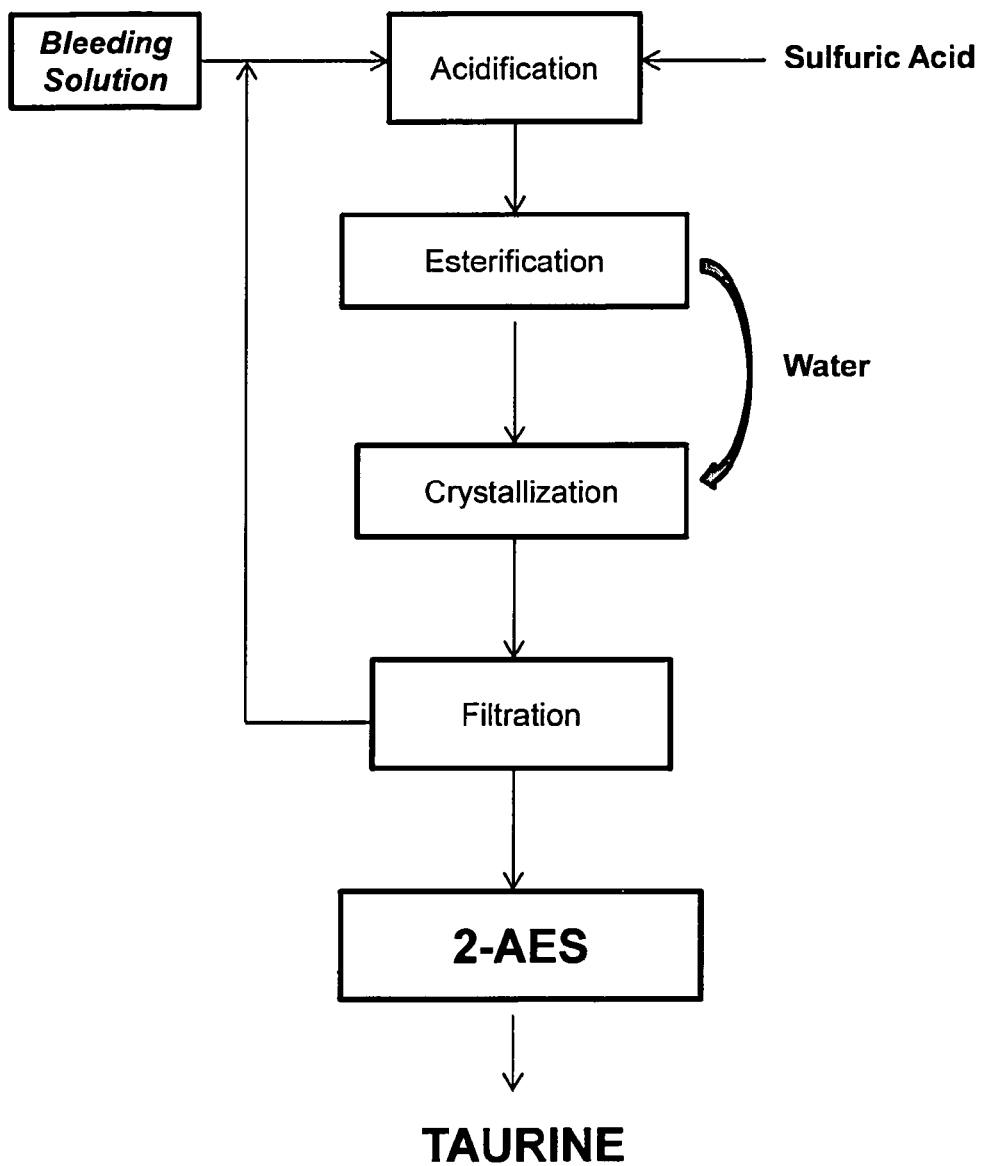
FIG. 2 is a flow chart showing the cyclic process for treating the bleeding waste solution wherein the residual MEA is converted to AES and therefore taurine.

The present inventor has carried out an extensive investigation with the object of providing a process for producing taurine which increases the overall yield to 95% or greater and eliminates the discharge of waste stream. This cyclic process is economical, industrially applicable, and environmentally friendly.

In the present invention, MEA is neutralized and esterified with sulfuric acid to yield 2-AES by any one of the many methods known in prior arts. The crude AES can be further purified by recrystallization or used as such. The yield for preparing the AES is generally more than 95% and nearly quantitative in a cyclic process.

Generally, the sulfonation temperature can be carried out from 90 to 150° C. At lower temperature, excessively long reaction time is required and becomes increasingly impractical. However, the higher temperature renders the reaction time shorter, but significantly lowers the yield, as the hydrolysis of AES is much faster than sulfonation. It is thus preferable to carry out the sulfonation reaction at a temperature from 100 to 130° C. The reaction is carried out under autogenous pressure or under increased pressure in a closed reactor to prevent the release of ammonia. In the sulfonation stage, AES is reacted with aqueous ammonium sulfite to yield taurine and ammonium sulfate as a byproduct. The amount of ammonium sulfite is not particularly limited. The suitable molar ratio of ammonium sulfite to AES is 1-5 times.

It is found after extensive investigation that there are two main competing reactions for AES in its reaction with sulfite salts in aqueous solution: sulfonation and hydrolysis of the sulfate ester, respectively, by sulfite group and water. The undesirable hydrolytic reaction is described as follows:

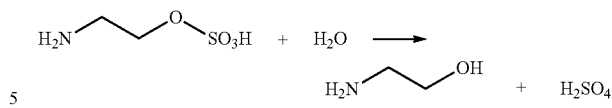

The hydrolysis of AES is accelerated under both acidic and basic conditions. It has now been found that the yield of taurine can be drastically increased by strictly maintaining the pH of reaction mixture from 6.0 to 8.0 and carrying out the sulfonation reaction at a temperature of 90 to 150° C.

The present invention discloses novel additives that can significantly increase the yield of taurine when added into the sulfonation reaction system by inhibiting the hydrolysis of AES. Suitable additives are aminoalcohols, such as MEA, diethanolamine, triethanolamine, N-methylethanolamine, N,N-dimethylethanolamine. These additives can be added to the reaction system, individually or in combination, at the start of the reaction in any amount, usually from 1% to 50%, preferably 1% to 10%. It is most preferable to use MEA as it is a byproduct from the hydrolysis of AES.

During the sulfonation, the pH of the reaction solution is found to decrease steadily with increasing formation of the main product, taurine, and byproduct, ammonium sulfate, which are acidic in nature. The side reaction, hydrolysis of AES to MEA and sulfuric acid, renders the solution even more acidic. When not controlled, the pH can be lowered from the initial 7.5 to 3.4 and a pungent smell of sulfur dioxide is released from the reaction system.

The pH during the sulfonation can be controlled by continuously dosing the reaction solution with a base. Both the common inorganic bases, such as sodium hydroxide and potassium hydroxide, and organic bases, such as alkylamines, aminoalcohols, can be used. It is, however, more preferable to use ammonium hydroxide or ammonium carbonate. In this way, no ions foreign to the reaction solution are introduced, thus simplifying the separation and purification process.

The pH during the sulfonation can be more conveniently maintained by using a buffering system. Any buffer compounds, known for the skilled in the art to be useful in the desired region of 6.0 to 8.0, such as phosphate, citrate, can be used. The present invention provides a much more preferable buffering system, which is comprised of weakly basic ammonium sulfite and weakly acidic ammonium bisulfite, ammonium sulfate, and taurine, because these components are present inherently in the reaction system. By using excess ammonium sulfite, i.e., more than 2 molar in excess, the pH of the reaction solution during the sulfonation process is only decreased from an initial 7.5 to a final 6.3.

The present invention discloses a process for the cyclic use of excess ammonium sulfite by simultaneously removing both taurine and byproduct ammonium sulfate from the reaction system. The mother liquor, consisting of the excess ammonium sulfite, residual taurine and AES, and some ammonium sulfate, is reinforced with just equal molar amount of ammonium sulfite and AES to start the next cycle of production.

The cyclic use of the mother liquor provides an added benefit since the mother liquor contains a small amount of MEA, an effective inhibitor for the hydrolysis of AES. The yield is significantly improved as the mother liquor is repeatedly recycled into the sulfonation stage.

As the concentration of MEA starts to accumulate in the mother liquor, a small portion is taken out from the reaction solution for further treatment. In general, up to 95% of the mother liquor can be recycled without adversely affecting the overall process. This bleeding waste solution of about 5-10% of the mother liquor contains dissolved taurine and nearly equal molar of MEA, as well as excess ammonium sulfite and some ammonium sulfate.

The present invention consequently provides a novel process for the treatment of this otherwise waste bleeding solution. It has been found that this bleeding solution can be acidified with sufficient quantity of sulfuric acid, which reacts with ammonium sulfite to yield ammonium sulfate and to release gaseous sulfur dioxide, recoverable as ammonium sulfite. The taurine and ammonium sulfate present in the bleeding waste solution are effectively recovered by crystallization.

It has now been found that the remaining MEA sulfate can be esterified by adding required amount of sulfuric acid and by heating to 150 to 170° C. while removing water under vacuum. After crystallizing from water, the obtained AES, along with residual taurine and ammonium sulfate can be purified or used directly to prepare taurine.

After the sulfonation stage, taurine is obtained as a solid mixture with ammonium sulfate. By use of their large difference in solubility, taurine and ammonium sulfate can be preferably separated by selective dissolution of ammonium sulfate in water. The amount of water is used in such an amount that is sufficient to dissolve ammonium sulfate but not too large to unnecessarily dissolve taurine. As a general rule, one more recrystallization of the crude taurine will yield a product of pharmaceutical grade.

It has now been found that from the mother liquor containing ammonium sulfate and a small amount of taurine, ammonium sulfate with less than 0.5% by weight of taurine can be recovered by crystallization. To that end the crystallization temperature should be taken above a minimum value, which depends on the weight ratio taurine/ammonium sulfate and the content of water. Generally, the crystallization temperature will be from 20 to 100° C., more preferably 30 to 60° C.

The recovery of ammonium sulfate, according to present invention, can be combined in various ways with the preparation of taurine. For example, if taurine is obtained in the form of an aqueous solution containing taurine and ammonium sulfate, the taurine can be removed initially from the solution by conventional crystallization techniques. Thereafter, ammonium sulfate can be recovered from the remaining solution by concentration, crystallization, and filtration. The mother liquor can then be returned to the taurine crystallization stage.

As an alternative, after the production of the aqueous solution containing ammonium sulfate and taurine, the ammonium sulfate can initially be recovered by the process of the invention to concentrate, crystallize, and filtrate. Thereafter, the remaining solution can be subjected to conventional crystallization technique to crystallize the taurine. The resulting solution can then be recycled to the ammonium sulfate separation stage.

The following examples will illustrate the practice of this invention but are not intended to limit its scope.

Comparative Example

In a one-liter autoclave equipped with a stirrer, 134 g of ammonium sulfite monohydrate and 300 mL of water were added. After the pH was adjusted to pH 7.2 with 6 N sulfuric acid, 106.7 g of AES was added. The mixture was stirred at 110° C. under autogenous pressure for 40 hours. When the autoclave was opened after the reaction, pungent smell of sulfur dioxide emerges and the pH of the reaction solution was found to be 3.9.

HPLC analysis indicated there remained 9% AES, 54% taurine, and 38% MEA.

Example 1

Into a one-liter autoclave equipped with a stirrer were charged 251 g of ammonium sulfite monohydrate and 300 mL of water. After the pH of the solution was adjusted to 7.2 with 6 N sulfuric acid, 106.7 g of AES was added. After the reaction was carried out at 110° C. under autogenous pressure for 24 hours, the pH was found to be 5.9.

HPLC analysis showed that the solution contains 67.5 g of taurine (72% theoretical yield), 3.2 g of unchanged AES (3%), and 11.4 g of MEA.

Example 2

Into a one-liter autoclave equipped with a stirrer were charged 251 g of ammonium sulfite monohydrate, 40 g of ammonium sulfate, 15.3 g of MEA, and 300 mL of water. After the pH of the solution was adjusted to 7.2 with 6 N sulfuric acid, 106.7 g of AES was added. After the reaction was carried out at 110° C. under autogenous pressure for 24 hours, the pH was found to be 6.2.

HPLC analysis showed that the solution contains 79 g of taurine (85% theoretical yield), 1.4 g of unchanged AES (1.3%), and 22.2 g of MEA.

Example 3

The reaction was carried the same as in Example 2, except diethanolamine was used in place of MEA.

HPLC analysis showed the reaction mixture contains 78 g of taurine (83% yield), 2.5 g of unchanged AES (5.5%), and 5.3 g (11.6%) of MEA.

Examples 4-8

These examples demonstrate the cyclic use of mother liquor in the preparation of taurine. Using the same one-liter autoclave, the starting materials given in the table were reacted at 120° C. for 18 hours. Afterwards, the solution is cooled to 10° C. to crystallize taurine and ammonium sulfate, which are filtered off and washed with a solution saturated with ammonium sulfate. The mother liquor is charged with ammonium sulfite monohydrate and then adjusted to pH 7.2 with aqueous ammonium hydroxide. AES is then charged and pH rechecked and if necessary readjusted to 7.2 with ammonium hydroxide or dilute sulfuric acid. The results are shown in the following table.

The solid filtrate, comprised of taurine and ammonium sulfate, from each batch, is combined and stirred as a suspension in water to dissolve ammonium sulfate. After filtration, crude taurine is washed with water and recrystallized from deionized water. Yield: 379.7 g (81.0%).

An additional 15.2 g (3.2%) of taurine is recovered from the mother liquor after recrystallization and separation of ammonium sulfate.

TABLE

Experimental Results of Example 4 to 8

| Example | Ammonium Sulfite Monohydrate | AES | Taurine (HPLC Assay) | Yield |
|---|---|---|---|---|
| Example 4 | 301.5 g | 106.7 g | 79.8 g | 85.1% |
| Example 5 | 110.6 g | 106.7 g | 77.2 g | 82.3% |

TABLE-continued

Experimental Results of Example 4 to 8

| Example | Ammonium Sulfite Monohydrate | AES | Taurine (HPLC Assay) | Yield |
|---|---|---|---|---|
| Example 6 | 115.2 g | 106.7 g | 81.4 g | 86.8% |
| Example 7 | 107.2 g | 106.7 g | 82.6 g | 88.1% |
| Example 8 | 108.4 g | 106.7 g | 80.2 g | 85.5% |

Example 9

The solution of the dissolved ammonium sulfate and the washings from Examples 4-8 is concentrated to a suspension of crystalline ammonium sulfate and then cooled to 60° C. The suspension is filtered and the isolated solid is washed with a solution saturated with ammonium sulfate. This yields 254 g of ammonium sulfate with 0.3% by weight of taurine. The white crystalline solid is suitable for fertilizer production.

Example 10

To a filtration mother liquor containing 65 g of MEA, 118 g of taurine, 5 g of AES, 180 g of ammonium sulfite, and 85 g of ammonium sulfate, was carefully added 325 g of sulfuric acid, while the formed gaseous sulfur dioxide was absorbed with ammonium hydroxide to yield a solution of ammonium sulfite. The solution was stirred and heated under vacuum distillation to remove water at bath temperature from 120 to 170° C. A clear white paste was obtained. After no more water was observed to distill from the flask, heating bath was removed and the flask was cooled to a semi-solid state. Then 350 mL of water was quickly added and the suspension was stirred at 50° C. for 30 minutes to obtain a crystalline suspension. Upon cooling to 15° C., the suspension was filtrated and washed with a little cold water. The filtrate is comprised of AES, taurine, and ammonium sulfate, weighed 119.2 g, 108.4 g, and 85.6 g each.

What is claimed is:

1. A cyclic process for increasing the overall production yield of taurine from monoethanolamine, comprising:
    (a) Reacting monoethanol amine with sulfuric acid to form 2-aminoethyl hydrogen sulfate ester;
    (b) Carrying out the reaction of 2-aminoethylhydrogen sulfate ester with ammonium sulfite to yield taurine in a buffering system at pH 6.0 to 8.0;
    (c) Suppressing the hydrolysis of 2-aminoethyl hydrogen sulfate ester during its reaction with ammonium sulfite by use of hydrolysis inhibitors;
    (d) Converting the residual monoethanolamine in the crystallization mother liquor of taurine to 2-aminoethyl hydrogen sulfate ester, which is recycled to step (a) to produce taurine.

2. The process according to claim 1, wherein the buffering system is composed of ammonium bisulfite and excess ammonium sulfite.

3. The process according to claim 1, wherein hydrolysis inhibitors are monoethanolamine, diethanolamine, triethanolamine, and dimethylaminoethanol.

4. The process according to claim 1, wherein the residual monoethanolamine in the crystallization mother liquor of taurine is reacted with sulfuric acid in the presence of ammonium sulfate to regenerate 2-aminoethyl hydrogen sulfate ester intermediate.

* * * * *